United States Patent
Raspagliesi

(10) Patent No.: US 8,962,011 B2
(45) Date of Patent: Feb. 24, 2015

(54) PROCESS AND INTRA-CERVICAL DEVICE FOR THE LOCAL RELEASE OF DRUGS IN THE LOCAL-REGIONAL TREATMENT OF CERVICAL CANCER

(75) Inventor: Francesco Raspagliesi, Milan (IT)

(73) Assignee: Fondazione IRCCS Istituto Nazionale Dei Tumori (IT)

( * ) Notice: Subject to any disclaimer, the term of this patent is extended or adjusted under 35 U.S.C. 154(b) by 266 days.

(21) Appl. No.: 13/146,362

(22) PCT Filed: Jan. 29, 2009

(86) PCT No.: PCT/IB2009/000151
§ 371 (c)(1),
(2), (4) Date: Jul. 26, 2011

(87) PCT Pub. No.: WO2010/086681
PCT Pub. Date: Aug. 5, 2010

(65) Prior Publication Data
US 2012/0020877 A1    Jan. 26, 2012

(51) Int. Cl.
*A61F 6/14* (2006.01)
*A61F 13/02* (2006.01)
*A61K 9/00* (2006.01)

(52) U.S. Cl.
CPC ............. *A61K 9/0039* (2013.01); *A61K 9/0036* (2013.01)
USPC ............ 424/432; 424/422; 424/423; 424/430

(58) Field of Classification Search
USPC ................. 424/422–425, 430, 432; 604/890.1
See application file for complete search history.

(56) References Cited

U.S. PATENT DOCUMENTS

| | | | |
|---|---|---|---|
| 4,069,307 A | | 1/1978 | Higuchi et al. |
| 4,126,024 A | * | 11/1978 | Timmons et al. ............... 70/233 |
| 4,249,531 A | | 2/1981 | Heller et al. |
| 5,224,493 A | | 7/1993 | Sawan et al. |
| 5,947,991 A | * | 9/1999 | Cowan .......................... 606/191 |
| 2003/0049302 A1 | * | 3/2003 | Pauletti et al. ................. 424/430 |

(Continued)

FOREIGN PATENT DOCUMENTS

| | | |
|---|---|---|
| DE | 2244923 A1 | 4/1974 |
| DE | 2424439 A1 | 12/1975 |

(Continued)

OTHER PUBLICATIONS

Xi Cheng et al (The prognosis of women with stage IB1-IIB node positive cervical carcinoma after radical surgery; World Journal of Surgical Oncology, 2004, 2; 47).*

(Continued)

*Primary Examiner* — Michael G Hartley
*Assistant Examiner* — Micah-Paul Young
(74) *Attorney, Agent, or Firm* — Schwegman Lundberg & Woessner, P.A.

(57) ABSTRACT

An intrauterine device and more specifically an intracervical device (ICD) for the local release of drugs in the loco-regional treatment of tumours of the uterine cervix comprises an elongated stem (2) to be positioned in the cervical canal (15), this stem consisting of an inner hollow core (3) and a coating (4) containing a gradual-release drug, the stem being attached to: a first element (5) for blocking the stem (2) inside the uterine cavity (12), and located at the cranial or upper end; a second blocking element (7, 71) positioned inside the vagina (11), against the ectocervix (16), located at the caudal or lower end of the stem (2).

22 Claims, 2 Drawing Sheets

(56) References Cited

U.S. PATENT DOCUMENTS

| | | | |
|---|---|---|---|
| 2004/0152978 A1* | 8/2004 | Duchon et al. | 600/431 |
| 2004/0247674 A1* | 12/2004 | Haapakumpu et al. | 424/471 |
| 2008/0069850 A1 | 3/2008 | Shalaby | |

FOREIGN PATENT DOCUMENTS

| | | | |
|---|---|---|---|
| WO | WO-99/22680 A1 | 5/1999 | |
| WO | WO-03/022260 A1 | 3/2003 | |

OTHER PUBLICATIONS

"International Application Serial No. PCT/IB2009/000151, International Search Report mailed Aug. 24, 2009", 4 pgs.

Abu, J., et al., "Endometrial adenocarcinoma following insertion of the levonorgestrel-releasing intrauterine system (mirena) in a 36-year old woman", *International Journal of Gynecological Cancer*, 16(3), (2006), 1445-1447.

* cited by examiner

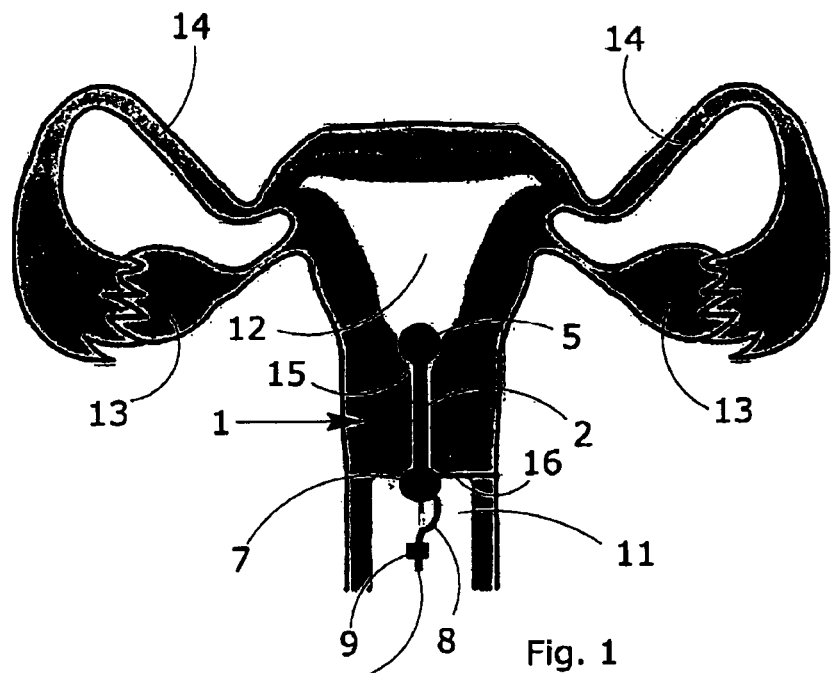
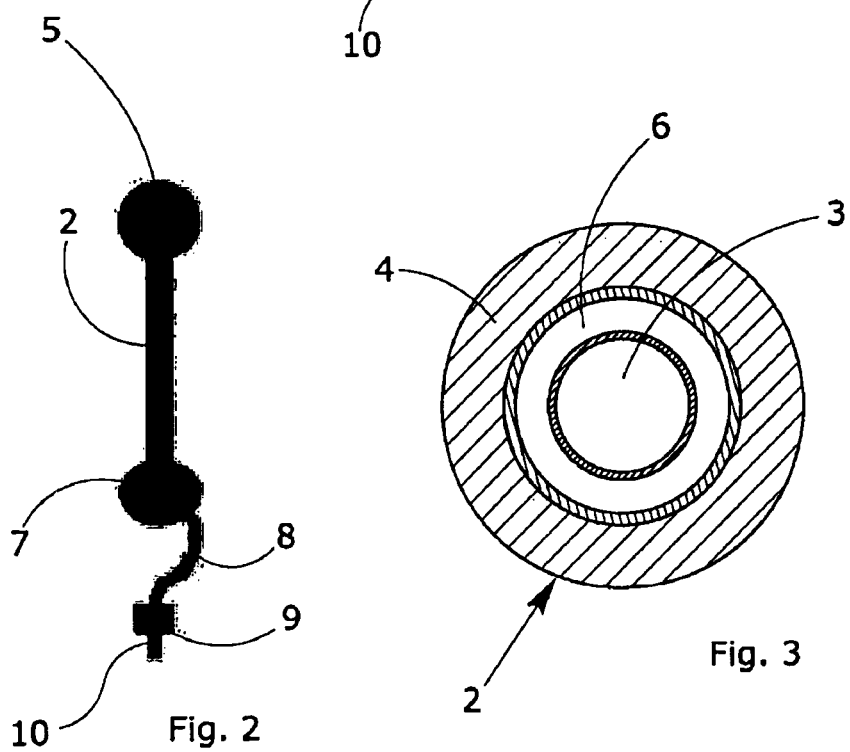

PROCESS AND INTRA-CERVICAL DEVICE FOR THE LOCAL RELEASE OF DRUGS IN THE LOCAL-REGIONAL TREATMENT OF CERVICAL CANCER

RELATED APPLICATIONS

This application is a nationalization under 35 U.S.C. 371 of PCT/IB2009/000151, filed Jan. 29, 2009 and published as WO 2010/086681 A1 on Aug. 5, 2010, which application and publication are incorporated herein by reference in their entirety.

TECHNICAL FIELD

This invention concerns an intrauterine device and more specifically an intracervical device (ICD) for the local release of drugs, in particular in the treatment of the uterine cervix. The invention also concerns process of loco-regional treatment of tumors of the uterine cervix.

More specifically, this invention refers to an intracervical device (ICD), the production and local implantation of which is designed to eliminate the problems connected with the systemic (intravenous) administration of certain specific drugs for tumours of the uterine cervix, and in particular to reduce their systemic side effects.

Another aim of this invention is to increase the concentration of the drug in the target area (cervix, parametria, lymph nodes) and thus to reduce the doses of drug necessary for the treatment of the disease.

The device according to the invention substantially comprises an elongated stem to be positioned in the cervical canal, consisting of an inner hollow core and a coating containing a gradual-release drug, together with a first element for blocking the stem inside the uterine cavity, positioned at the cranial or upper end of the stem, and a second blocking element positioned inside the vagina, against the ectocervix, located at the caudal or lower end of the stem.

This invention can be applied in the medical field and in particular in the sector of medical type devices that can be implanted for the administration of drugs.

BACKGROUND ART

As is known, carcinoma of the uterine cervix (CUC) is the second most frequent gynaecological tumour in industrialised countries and the main cause of death in the female population in developing countries.

Despite the possibility of effective secondary prevention (pap test), tumours of the uterine cervix are the cause of around 4800 deaths every year in the United States, while in Italy around 3700 new cases and 1700 deaths are recorded every year.

Surgery represents the treatment of choice in the initial stages of the disease, that is to say when the tumour is confined to the neck of the uterus. In these stages, surgery can be followed by post-operative treatment based on various prognostic factors such as the dimensions of the tumour and the presence of any lymph node metastases.

In the more advanced stages, radiotherapy combined with appropriate chemotherapy is currently considered as the standard treatment.

Pre-operative (or neoadjuvant) chemotherapy for the treatment of locally advanced carcinoma of the cervix has two different objectives:
a) to reduce the local extent of the disease in order to allow surgery which would not otherwise be possible;
b) to cure any neoplastic emboli which have spread from the tumour to parts of the body remote from the primary tumour.

Recent meta-analyses of the randomized studies published to date on neoadjuvant chemotherapy have demonstrated a significant therapeutic benefit of this treatment, with a reduction in mortality risk of 36%.

In almost all the studies published so far, the drugs are administered intravenously and only in some studies intra-arterially. Intravenous administration of drugs leads to the onset of toxic systemic effects which differ according to the drugs used.

The main drugs that have proved to be effective in the treatment of CUC are as follows in decreasing order of importance (the main toxic effects are indicated in brackets):
Cisplatin (nausea, vomiting, nephrotoxicity, neurotoxicity, myelotoxicity);
Taxol (nausea, vomiting, alopecia, myelotoxicity);
Ifosfamide (nausea, vomiting, myelotoxicity, nephrotoxicity);
Topotecan (nausea, vomiting, myelotoxicity);
Carboplatin (nausea, vomiting, myelotoxicity);
Adriamycin (nausea, vomiting, alopecia, cardiotoxicity);
Irinotecan (nausea, vomiting, gastrointestinal toxicity, myelotoxicity);
Gemcitabine (nausea, vomiting, myelotoxicity);
Bleomycin (nausea, vomiting, cutaneous toxicity, pulmonary fibrosis).

It has been demonstrated that systemic (intravenous) administration of these drugs causes the side effects described above.

DESCRIPTION OF THE INVENTION

This invention proposes to provide a device and a process which can eliminate the problems connected to the systemic (intravenous) administration of these drugs, and in particular to reduce the systemic side effects.

Another aim is to increase the concentrations of the drug in the target area (cervix, parametria, lymph nodes) and thus reduce the doses of drug necessary for the treatment of the disease.

These aims are achieved by the invention which proposes an intrauterine device with slow drug release, presenting the features of the attached independent claim 1.

Advantageous embodiments of the invention are described in the dependent claim.

The device according to the invention substantially comprises:
an elongated stem to be positioned in the cervical canal, preferably cylindrical in shape and comprising an inner hollow core made from plastic material coated with a layer of polymer or similar material, containing the active ingredient, able to determine the slow local release of the selected drug;
a first element for blocking the stem and positioned inside the uterine cavity, consisting of a silicone ball located at the cranial or upper end of the stem and in communication with its inner cavity;
a second blocking element positioned inside the vagina, against the ectocervix, located at the caudal or lower end of the stem and in communication with its inner cavity;
a connecting tube with a standard connector for disposable syringes at its free end and in communication with the cranial blocking element/elongated stem/caudal blocking element system.

This second blocking element is in the shape of a ball if the device is intracervical, that is to say with release of the active ingredient only inside the cervical canal, or in the shape of a cup made from plastic material with the concave part in contact with the ectocervix coated with a layer of polymer or similar material for the gradual release of the active ingredient if the device is both ecto- and intracervical.

Advantageously, the hollow core is between 2 and 3 cm in length and between 2.0 and 3.5 mm in diameter, while the diameter of the coating layer varies between 3.0 and 6.0 mm. The diameter of the balls, inflated with water and/or air, is between 3.0 and 3.5 mm, while the diameter of the coated cup varies between 1.5 and 5.0 cm.

The possible uses of the device according to the invention in the treatment of tumours of the uterine cervix include:
 carcinoma of the uterine cervix stage Ia2-Ib1: to reduce the invasive nature of surgery and to make it possible, in some cases, to preserve the organ (conservative treatment) and maintain reproductive function;
 carcinoma of the uterine cervix stage Ib2-II: neoadjuvant chemotherapy followed by radical surgery;
 carcinoma of the uterine cervix stage Ib2-IV: chemotherapy associated with radiotherapy.

The device can also be used for contraceptive purposes. In this case, the device will be designed to release substances inside the cervical canal that can block the motility of the spermatozoa or to cause cell death.

DESCRIPTION OF THE DRAWINGS

Other features and advantages of the invention will become evident on reading the following description of one embodiment of the invention, provided as a non-binding example, with the help of the accompanying drawings, in which:

FIG. 1 is a schematic view of the device according to the invention, in a first embodiment, designed for the intracervical release of drugs (tumours of the cervical canal—use for contraceptive purposes), and in its working position;

FIG. 2 is a detailed schematic of the stem of the device shown in FIG. 1;

FIG. 3 is an enlarged cross-section of the stem of the device shown in FIG. 1;

DESCRIPTION OF ONE EMBODIMENT OF THE INVENTION

Figure 4:
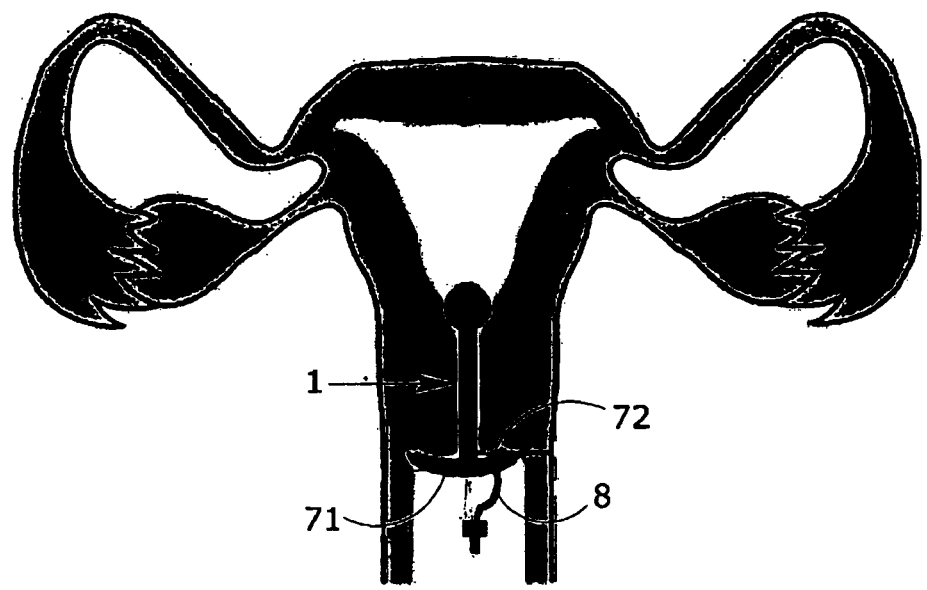
FIG. 4 is a schematic view of the device according to the invention, in a second embodiment, designed for the ecto-endocervical release of drugs (tumours of the ectovervix), in its working position.

With reference to these figures, and for the moment in particular to FIGS. 1, 2 and 3, the first embodiment of the device according to the invention is briefly described.

This device, indicated overall with the reference number 1, comprises an elongated stem 2, preferably cylindrical, consisting of an inner hollow core 3, made for example from plastic material, and a coating of polymer or similar material 4 able to gradually release a drug contained within it.

At the free end of the stem 2, which will be called the cranial or upper end, is a blocking element 5 consisting of an inflatable silicone ball, the cavity of which communicates with the inner cavity 6 of the core 3 of the stem 2.

At the other end of the stem 2, which will be called the caudal or lower end, is a second blocking element 7, also in the form of an inflatable silicone ball and also communicating with the inner cavity 6 of the core 3 of the stem.

The ball 7 is attached to a connecting tube 8 fitted with a check valve 9 and, at its free end 10, a standard connector for disposable syringes for inflation of the balls 5 and 7 with water and/or air.

The tubular core 3 is between 2 and 3 cm in length and between 2.0 and 3.5 mm in diameter, while the diameter of the coating 4 containing the active ingredient varies between 3.0 and 3.5 mm. The diameter of the inflated balls 5 and 7 can vary between 3 and 6 mm.

FIG. 1 is a schematic view of the intracervical device shown in FIG. 2 in position.

In particular, this figure schematizes the essential parts of the female reproductive organs: the vagina 11, the uterine cavity 12, the ovaries 13, the uterine tubes 14, the cervical canal 15, the ectocervix 16.

As can be seen, the device 1 is positioned in such a way that the elongated stem 2 is placed in the cervical canal with the first blocking ball 5 inside the uterine cavity and the second blocking ball 7 inside the vagina 11, against the ectocervix 16. In FIG. 1, the balls 5 and 7 are shown already inflated to hold the device firmly in position, for the gradual release inside the cervical canal of the drug contained in the coating 4 of the stem 2. The cavity 3 of the stem 2 allows the passage of menstrual blood when the device is in place.

Figure 5:
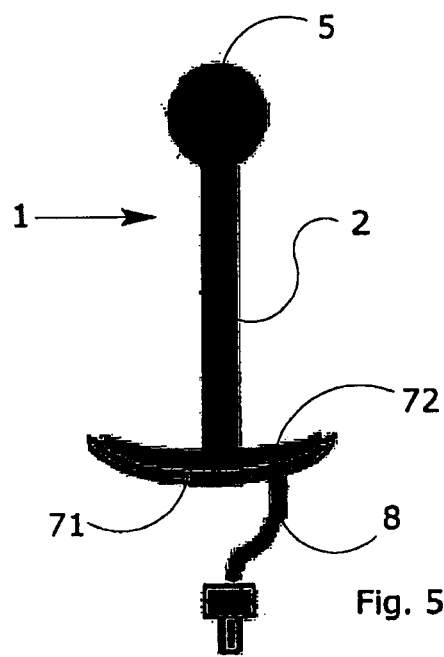
FIG. 5 shows a detailed view of the device shown in FIG. 4.

With reference now to FIGS. 4 and 5, the second embodiment of the device according to the invention is described, this being designed for ecto-endocervical release of drugs to cure tumours of the ectocervix.

In the description which follows, the same reference numbers will be used to distinguish the same or corresponding elements with respect to the first embodiment.

As can be seen in FIG. 5, the device according to the invention, indicated overall again with the reference number 1, differs from the device shown in FIG. 2 merely in the shape of the second blocking element 7, which instead of consisting of an inflatable ball consists of a cup 71 made from plastic, silicone or other material, coated on its concave surface facing the stem 2 with a disc 72 which is also concave and made from polymeric or similar material, able to determine the slow local release of the chosen drug, like the coating 4 of the stem 2.

The dimensions of the device 1 shown in FIG. 5 correspond to those of the device shown in FIG. 2, the diameter of the disc 72 containing the active ingredient varying between 1.5 and 5 cm.

The inflation tube 8 passes through the cup 71 and, in this case too, communicates with the inner cavity 6 of the core 3 of the stem 2, as can be seen in FIG. 3, which is copied from the previous page for convenience.

FIG. 4, almost the same as FIG. 1, shows the device illustrated in FIG. 5 in place.

As can be seen, the concave surface of the polymeric disc 72 of the second blocking element 7 comes into contact with the ectocervix, determining a gradual release of the drug it contains in this zone, in addition to the release in the cervical canal by the coating of the stem 2.

Some of the therapeutic substances that can be used with the device according to the invention are listed below:
 1. Chemotherapy Drugs.
 Cisplatin, Carboplatin, Taxol, Taxotere, Topotecan, Irinotecan, Adriamycin, Gemcitabine, Bleomycin, Ifosfamide, Vinorelbine, 5 Fluorouracil, VP 16, Metrotrexate, Mitomycin C, Vincristine, Vinblastine.
 2. Drugs for "Targeted Therapy".
 The progress in molecular biology, culminating with the complete sequencing of the three billion bases of the human genome, has opened a new era for molecular oncology by providing a totally new method for the treatment of cancer. On the basis of the evidence that many of the protein products of oncogenes or suppressor genes are carriers of "information", the systematic analysis of the different expression of these genes in normal tissues with respect to those that develop in tumour tissues (i.e. the genomic-functional approach) has become one of the most universally used strategies for the discovery of the molecular circuits involved in uncontrolled proliferative phenomena. By knowing many of the molecular events which are altered in certain types of tumours, pharmacological research and pharmacogenomic studies already make it possible to identify and design targeted drugs which, alone or in combination with chemo-, radio-, or hormonotherapy, attack the altered molecules and not just the proliferative ones, making it possible in some—for the moment limited—cases to fight the tumour directly.

3. Compounds for Radio-Immunotherapy.

Monoclonal antibodies (MoAbs) are directed against a specific antigen expressed on the neoplastic cells; some MoAbs are bound to a radioactive molecule (radioactive isotopes such as, for example, iodine 131, yttrium 90,etc.) which acts directly on the neoplastic cell. Many studies are currently in progress, aimed at extending the applications and synthesizing new ones.

4. Radio-labelled compounds for possible use in the techniques for identification of sentinel lymph nodes.

The invention is obviously not limited to the particular embodiments described above and illustrated in the accompanying drawings. Numerous specific modifications can be made which are within the experience of technicians working in this sector, without departing from the scope of the invention, defined by the attached claims.

5. Use of the Intracervical Device for contraception.

The polymeric material of the device can be used for the local release of substances with a spermatocide effect. In this case, the device can be used as a contraceptive that can, without hormonal type substances, have a marked contraceptive effect, preventing the cellular elements of the sperm (spermatozoa) from reaching the tubes and fertilising the egg.

The invention is described above with reference to a preferred embodiment. It is nevertheless clear that the invention is susceptible to numerous variations which lie within its scope, within the framework of technical equivalents.

The invention claimed is:

1. An intracervical device (ICD) for the local release of drugs in the loco-regional treatment of tumors of the uterine cervix, comprising:
    an elongated non-inflatable stem configured to be positioned in the cervical canal, this stem having a coating containing a gradual-release drug,
    a first blocking element attached to the stem, configured for blocking the stem inside the uterine cavity and located at the cranial or upper end of the stem;
    a second blocking element attached to the stem and configured to be positioned inside the vagina, against the ectocervix, located at the caudal or lower end of the stem, wherein the first blocking element is an inflatable ball in communication with a cavity of an inner hollow core of the stem, wherein a connecting tube which passes through the second blocking element and communicates with the cavity allows for inflation of the ball.

2. An intracervical device according to claim 1, wherein the second blocking element is an inflatable ball.

3. An intracervical device according to claim 1, wherein the second blocking element comprises a cup coated on its concave surface facing the stem with a disc which is also concave containing a gradual release drug.

4. An intracervical device according to claim 1, wherein the coating of the stem and the coating of the second blocking element containing a gradual-release drug comprise polymeric material.

5. An intracervical device according to claim 1, wherein the stem is substantially cylindrical in shape and wherein the stem is between 2 and 3 cm in length, the inner core having a diameter between 2.0 and 3.5 mm, while the coating varies between 3.0 mm and 3.5 mm in diameter.

6. An intracervical device according to claim 1, wherein the diameter of the first ball varies, when inflated, between 3 and 6 mm.

7. An intracervical device according to claim 2, wherein the diameter of the second ball varies, when inflated, between 3 and 6 mm.

8. An intracervical device according to claim 2, wherein the diameter of the disc of the second blocking element varies between 1.5 and 5.0 cm.

9. An intracervical device according to claim 1, comprising a connecting tube configured for inflating the ball of the first blocking element the connecting tube passing through the second blocking and being fitted with a check valve.

10. An intracervical device according to claim 1, wherein the gradual-release drug is one of: a drug for target therapy, Cisplatin, Carboplatin, Taxol, Taxotere, Topotecan, Irinotecan, Adriamycin, Gemcitabine, Bleomycin, Ifosfamide, Vinorelbine, 5 Fluorouracil, VP 16, Metrotrexate, Mitomycin C, Vincristine, Vinblastine, a compound for radio-immunotherapy or a radio-labelled for identification of sentinel lymph nodes.

11. An intracervical device according to claim 1, wherein the gradual-release drug comprises a spermatocide suitable for contraception.

12. A process of loco-regional treatment of tumors of the uterine cervix comprising the steps of:
    providing an intracervical device comprising an elongated stem of cylindrical shape having an inner hollow core and a coating containing a gradual-release chemotherapeutic drug, wherein the intracervical device comprises a first blocking element attached to the stem at the cranial or upper end, and a second blocking element attached to the stem located at the caudal or lower end of the stem, the first blocking element comprising a first inflatable ball;
    positioning the device with the stem in the cervical canal of a female, with the first blocking element inside the uterine cavity and with the second blocking element inside the vagina, against the ectocervix, wherein the positioning includes inflating the first inflatable ball without inflating the stem to form a first blocking ball inside the uterine cavity while the stem keeps its cylindrical shape; and
    locally releasing the chemotherapeutic drug from the coating to the uterine cervix.

13. An intracervical device according to claim 1, wherein the gradual release drug is a drug for targeted therapy.

14. An intracervical device according to claim 1, wherein the gradual release drug is one of: a compound for radio-immunotherapy and a radio-labeled compound for identification of sentinel lymph nodes.

15. A process of loco-regional treatment of tumors of the uterine cervix comprising the steps of:
    providing an intracervical device comprising an elongated stem having an inner core and a coating containing a gradual-release chemotherapeutic drug, wherein the intracervical device comprises a first blocking element attached to the stem at the cranial or upper end, and a second blocking element attached to the stem located at the caudal or lower end of the stem, the first blocking element comprising a first inflatable ball;

positioning the device with the stem in the cervical canal of a female, with the first blocking element inside the uterine cavity and with the second blocking element inside the vagina, against the ectocervix, wherein positioning includes inflating the first inflatable ball to form a first blocking ball inside the uterine cavity; and locally releasing the chemotherapeutic drug from the coating to the uterine cervix; wherein the stem is not inflated during positioning of the device and allows the passage of menstrual blood when the device is in position.

16. The intracervical device of claim 1, wherein the stem is configured to allow passage of menstrual blood when the stem is positioned in the cervical canal.

17. The intracervical device according to claim 16 wherein the stem comprises two cavities one in communication with the inflatable ball and one configured to allow said passage of menstrual blood.

18. A process according to claim 15 wherein the gradual release chemotherapeutic drug comprises one or more chemotherapy drugs selected in the group of: Cisplatin, Carboplatin, Taxol, Taxotere, Topotecan, Irinotecan, Adriamycin, Gemcitabine, Bleomycin, Ifosfamide, Vinorelbine, 5 Fluorouracil, VP 16, Metrotrexate, Mitomycin C, Vincristine, Vinblastine.

19. A process according to claim 15 wherein the coating comprises a layer of polymer material containing said chemotherapeutic drug, the coating being configured to determine a slow local release of the chemotherapeutic drug.

20. A process according to claim 15 wherein the second blocking element comprises a second inflatable ball and wherein the step of positioning comprises inflating the second inflatable ball.

21. A process according to claim 15 wherein the second blocking element is in the shape of a cup with a concave part designed to act in contact with the ectocervix and coated with a gradual release chemotherapeutic drug, the process comprising locally releasing the chemotherapeutic drug from the coating to the uterine cervix and to the ectocervical area.

22. A process according to claim 15, wherein the locoregional treatment of tumors include treatment of the following tumors of the uterine cervix: carcinoma of the uterine cervix stage Ia2-Ib1; carcinoma of the uterine cervix stage Ib2-II; carcinoma of the uterine cervix stage Ib2-IV.

* * * * *